United States Patent [19]

Kozachuk

[11] Patent Number: 5,942,540
[45] Date of Patent: Aug. 24, 1999

[54] METHODS OF PROVIDING SYMPTOMATIC AND PROPHYLACTIC NEUROPROTECTION

[76] Inventor: Walter E. Kozachuk, 11403 Cam Ct., Kensington, Md. 20895-1313

[21] Appl. No.: 08/948,319

[22] Filed: Oct. 10, 1997

Related U.S. Application Data

[63] Continuation-in-part of application No. 08/632,338, Apr. 10, 1996, Pat. No. 5,728,728.

[51] Int. Cl.$^6$ .......................... A61K 31/27; C07C 271/10
[52] U.S. Cl. ............................................ 514/483; 560/158
[58] Field of Search .................................. 514/909, 534, 514/483; 560/164, 158

[56] References Cited

U.S. PATENT DOCUMENTS

| 5,256,690 | 10/1993 | Sofia ....................................... 514/483 |
| 5,728,728 | 3/1998 | Kozachuk ............................... 514/483 |

OTHER PUBLICATIONS

"Abnormalities of Striatal Projection Neurons and N-Methyl-D-Aspartate Receptors in Presymptomatic Huntington's Disease" by Albin, et. al. Brief Report, vol. 322, No. 18, May 1990. vol. 322, pp. 1293–1298.

"Alternative Excitotoxic Hypotheses" by Albin, et. al., Neurology, Apr. 1992. vol. 42, pp. 733–738.

"Amino Acid Abnormalities In Epileptogenic Foci" by Perry, et. al., Neurology, Jul. 1981. vol. 31, pp. 872–876.

"B–Amyloid Peptides Destabilize Calcium Homeostasis and Render Human Cortical Neurons Vulnerable to Excitotoxicity" by Mattson, et. al., The Journal of Neuroscience, Feb. 1992, vol. 12, pp. 376–388.

"B–Amyloid Protein Increases The Vulnerability of Cultered Cortical Neurons to Excitotoxic Damage" by Koh, et. al, Brain Research, 1990, vol. 533, pp. 315–320.

"Behaviorial Effects of Felbamate In Childhood Epileptic Encephalopathy (Lennox–Gastaut Syndrome)" by Gay, et. al., Psychological Reports, 1995, vol. 77, pp. 1208–1210.

"Ca2+–Dependant And Ca2+– Independent Glutamate Release, Energy Status and Cytosolic Free Ca2+ Concentration in Isolated Nerve Terminals Following Metabolic Inhibition: Possible Relevance to Hypoglycaemia and Anoxia" by Kauppinen, et. al., Neuroscience, vol. 27 No. 1, pp. 175–182, 1988.

"Chemically Induced Hypoglycemia and Anoxia: Relationship to Glutamate Receptor–Mediated Toxicity in Retina" by Zeevalk, et. al., Therapeutics, vol. 253, No. 3, Mar. 1990. pp. 1285–1292.

"Consequences of Epileptic Activity In Vitro" by Thompson, Brain Pathology 3, 1993. pp. 413–419.

"Does Impairment of Energy Metabolism Result in Excitotoxic Neuronal Death in Neurodegenerative Illnesses?" by Beal, American Neurological Assoc., 1992. vol. 31, pp. 119–130.

"Effects of Felbamate on Muscarinic and Metabotropic–Glutamate Agonist–Mediated Responses and Magnesium–Free or 4–Aminopyridine–Induced Epileptiform Activity in Guinea Pig Olfactory Cortex Neurons In Vitro" by Libri, et. al., Jour. of Pharm. & Exper. Thera., 1996, vol. 277, pp. 1759–1769.

"Excess Glutamate Levels in the Crebrospinal Fluid Predict Clinical Outcome of Bacterial Meningitis" by Spranger, et. al., Arch Neurol, vol. 53, Oct. 1996, pp. 992–996.

"Excitatory Amino Acid Neurotoxicity at the N–Methyl–D–Aspartate Receptor in Cultured Neurons: Role of the Voltage–Dependent Magnesium Block" by Cox, et. al., Brain Research, 1989, vol. 499, pp. 267–272.

"Excitatory Amino Acids Are Elevated in Human Epileptic Cerebral Cortex" by Sherwin, et. al., Neurology, Jun. 1988, vol. 38 pp. 920–923.

"Excitoprotective Effect of Felbamate in Cultured Cortical Neurons" by Kanthasamy, et. al., Brain Research, 1995, vol. 705, pp. 97–104.

"Excitotoxicity and Selective Neuronal Loss in Epilepsy" by Meldrum, Brain Pathology, 1993. vol. 3, pp. 405–412.

"Blutamate Becomes Neurotoxic Via the N–Methyl–D–Aspartate Receptor when Intracellular Energy Levels are Reduced" by Novelli, et. al., Brain Research, 1988. vol. 451, pp. 205–212.

"Evidence that Local Non–NMDA Receptors Contribute to Functional Deficits in Contusive Spinal Cord Injury" by Wrathall, et. al., Brain Research, 1992, vol. 586, pp. 140–143.

"Familial Increase in Plasma Glutamic Acid in Epilepsy" by Janjua, et. al., Epilepsy Research, 1992. vol. 11, pp. 37–44.

"Felbamate–Associated Fatal Acute Hepatic Necrosis" by O'Neil, et. al., The American Academy of Neurology, 1996.

"Felbamate Overdoese: A Case Report and Discussion of a New Antiepileptic Drug" by Nagel, et. al., Pediatric Emergency Care, 1995, vol. 11, pp. 369–371.

"Felbamate as Add–On Therapy" by Li, et. al., European Neurology, 1996, vol. 36, pp. 146–148.

"Felbamate Inhibits Dihydropyridine–Sensitive Calcium Channels in Central Neurons" by Stefani, et. al., Journal of Pharmacology and Experimental Therapeutics, vol. 277, No. 1, 1996, pp. 121–127.

"Felbamate Neuroprotection Against CA1 Traumatic Neuronal Injury" by Wallis, et. al., European Jouranl of Pharmacology, 1995, vol. 294 pp. 475–482.

"Felbamate Monotherapy has Stimulant–like Effects in Patients with Epilepsy" by Ketter, et. al., Epilepsy Research, 1996, vol. 23, pp. 129–137.

(List continued on next page.)

Primary Examiner—Alan L. Rotman
Assistant Examiner—Charanjit S. Aulakh
Attorney, Agent, or Firm—Joseph A. Rhoa

[57] ABSTRACT

Methods are disclosed for prophylactically and chronically preventing symptomatic depression, neuronal cell injury and cell death in systemic and neurological conditions, populations with cerebrovascular risk factors, and invasive vascular procedures, employing a glycine-site antagonist at the NMDA (N-methyl-D-aspartate) complex e.g., 2-phenyl-1,3-propanediol dicarbamate (felbamate).

2 Claims, No Drawings

OTHER PUBLICATIONS

"Mechanisms of Excitotoxicity in Neurologic Diseases" by Beal, The FASEB Journal, vol. 6, Dec. 1992, pp. 3338–3344.

"Mesial Temporal (Ammon's Horn) Sclerosis as a Common Cause of Epilepsy Aetiology, Treatment, and Prevention" by Falconer, The Lancet, Sep. 1974 pp. 767–770.

N–Methyl–D–Aspartate Receptor Plasticity in Kindling: Quantitative and Qualitative Alternations in the N–Methyl–D–Aspartate Receptor—Channel Complex, by Yeh, et. al., Proc. Natl. Acad. Sci., vol. 86, pp. 8157–8160, Oct. 1989.

"Mitochondrial Impairment Reduces the Threshold for in Vivo NMDA–Mediated Neuronal Death in the Striatum" by Simpson, et. al., Experimental Neurology 121, pp. 57–64, 1993.

"Neurotoxicity at the N–Methyl–D–Aspartate Receptor in Energy–Compromised Neurons" by Henneberry, et. al., Annals New York Academy of Sciences, pp. 225–233.

"Quinolinic Acid in Cerebrospinal Fluid and Serum in HIV–1 Infection: Relationship to Clinical and Neurological Status" by Heyes, et. al., Amer. Neurological Assoc., 1991 vol. 29, pp. 202–207.

"The Role of Excitatory Amino Acids and NMDA Receptors in Traumatic Brian Injury" by Faden, et. al., Science vol. 244, May 1989, pp. 798–800.

"Secretion of Neurotoxins by Mononuclear Phagocytes Infected with HIV–1" by Giulian, et. al., Reports, Dec. 1990. pp. 1593–1596.

"The Severity of Naloxone–Preciitated Opiate withdrawal is Attenuated by Felbamate, a Possible Glycine Antagonist" by Kosten, et. al., Neuropsychopharmacology, vol. 13, No. 4, 1995 pp. 323–333.

"The Glycine Site on the NMDA Receptor: Structure–Activity Relationships and Therapeutic Potential" by Leeson, et. al., Journal of Medicinal Chemistry, vol. 37, No. 24, Nov., 1994.

"Glycine Antagonists: Regulation of the NMDA Receptor–Channel Complex by the Strychnine–Insensitive Glycine Site" by Carter, Drugs of the Future 1992.

"Neuroprotection with Felbamate: a 7– and 28–day Study in Transient Forebrain Ischemia in Gerbils" by Shuaib, et. al., Brain Research 727, 1996.

"Posthypoxic Treatment with Felbamate is Neuroprotective in a Rat Model of Hypoxia–ischemia" by Wasterlain, Neurology 43, Nov. 1993.

"Felbamate Monotherapy for Partial–Onset Seizures: An Active–Control Trial" by Faught, et. al., Neurology 43, Apr., 1993.

"Reduction of Functional Neuronal Connectivity in Long–Term Treated Hypertension" by Mentis, Stroke, vol. 25, No. 3, Mar., 1994.

"Felbamate Monotherapy: Controlled Trial in Patients with Partial Onset Seizures" by Sachdeo, et. al., American Neurological Assoc., 1992.

"Felbamate Protects CA1 Neurons from Apoptosis in a Gerbil Model of Global Ischemia" by Wasterlain, et. al.

"Muscle Relaxant Action of Excitatory Amino Acid Antagonists" by Schwartz, et. al., 1993.

"Efficacy of Felbamate in Therapy for Partial Epilepsy in Children" by Carmant, et. al., The Journal of Pediatrics, Sep., 1994.

"Prophylactic Neuroprotection for Cerebral Ischemia" by Fisher, Stroke, vol. 25, No. 5, May, 1994.

"Brain Atrophy in Hypertension—A Volumetric Magnetic Resonance Imaging Study" by Salerno, et. al., Hypertension, vol. 20, No. 3, Sep., 1992.

5,942,540

METHODS OF PROVIDING SYMPTOMATIC AND PROPHYLACTIC NEUROPROTECTION

This is a continuation-in-part of application Ser. No. 08/632,338 filed Apr. 10, 1996, now U.S. Pat. No. 5,728,728, the disclosure of which is incorporated herein by reference.

FIELD OF THE INVENTION

The present invention relates to pharmaceutical compositions whose mechanisms of action include at least antagonism at the glycine site on the NMDA (N-methyl-D-aspartate) receptor complex, and to methods for prophylaxis, attenuation, or prevention of acute or chronic neuronal damage in various systemic or neurological diseases, conditions, or procedures.

BACKGROUND OF THE INVENTION

The major excitatory neurotransmitters in the central nervous system is L-glutamine and L-aspartate. Classification of the excitatory receptors include the AMPA, kainate and NMDA receptors. The NMDA receptor is located on the neuronal cell surface and is composed of multiple binding sites which regulate $Ca^{++}$ homeostasis. The glycine and glutamate binding sites are allosterically linked at the NMDA receptor complex. Glutamate is the principal excitatory neurotransmitter in the brain and has an integral role in neurologic function including cognition, memory, movement and sensation. Glutamate has also been implicated in the pathogenesis of multiple acute and chronic neurological diseases.

Felbamate (2-phenyl-1,3-propanediol dicarbamate) is a known pharmaceutical compound and is described in U.S. Pat. No. 2,884,444. Felbamate has multiple actions on the nerve cell of which one is a glycine site antagonist at the NMDA receptor. See U.S. Pat. Nos. 4,978,680; 5,082,861; 5,292,772; 4,868,327; and 5,256,690.

Felbamate is a modulator of NMDA function by a glycine site antagonist mechanism but has multiple mechanisms of action. These include interaction at the AMPA/kainate receptor, facilitating GABA function, modulation of the Na+ channel, interaction at both of the metabotropic and muscarinic receptors, as well as the L-type calcium channel.

Excessive stimulation of the NMDA receptor by excitatory amino acids or neurotoxic mediators of inflammation is believed to be the etiology of multiple acute and chronic neurological diseases. Sudden toxic elevations of glutamate in acute neurological disorders or increased nerve cell vulnerability by abnormal bioenergetic metabolism in chronic disorders are possible mechanisms. Thus, NMDA exictotoxicity may represent a final common pathway for neuronal death in both acute and chronic neurological disease.

Subsequent to the approval of Felbamate, in 1994 there were reports of aplastic anemia and hepatic failure. These adverse events may have been due to drug interaction.

OBJECT OF THE INVENTION

One of the objects of the present invention is to provide compositions and methods for the treatment of acute and chronic disorders that involve excessive activation of the NMDA receptor.

Another object of the present invention is to provide a method for attenuation or prevention of neuronal cell death caused by excessive activation of the NMDA receptor by administering the drug prophylactically and chronically when the patient has asymptomatic or pre-clinical systemic or neurological disease.

Another object of the present invention is to provide compositions and methods effective to prevent, control, or attenuate acute and chronic neuronal injury and death from systemic or neurological disease.

A further objective of the present invention is to provide compositions and methods for the prevention and control of acute and chronic systemic or neurological disorders that involve excessive activation of the NMDA receptor, which compositions are relatively non-toxic, have a high degree of effectiveness and continue to produce a therapeutic response over a long duration of time.

An additional object of the present invention is the treatment of the chronic neulogical condition called spasticity by the administration of a compound that has at least the property of antagonizing the glycine-site at the NMDA receptor.

SUMMARY OF THE INVENTION

The subject invention relates to methods for treating acute and chronic neurological diseases and reducing or preventing neuronal cell death in both systemic and neurological diseases, in mammals including humans, employing a drug whose mechanism of action is at least partially mediated through a strychnine-insensitive glycine receptor mechanism. The antagonists are administered intravenously or-orally, acutely or chronically, to prevent or attenuate neuronal damage and death. Advantageously, the drug is administered prophylactically and chronically when the patient is at risk for asymptomatic or pre-clinical systemic or neurological disease, or when the patient undergoes a vascular procedure which have a high risk for neuronal cell injury or death.

This invention also relates to a method of reducing or preventing neuronal cell injury or death when the glycine-site antagonist, felbamate, is administered prophylatically and chronically in a mammal, or a human.

This invention also relates to a method of reducing or preventing neuronal cell injury or death when the glycine-site antagonist, felbamate, is used as monotherapy or polytherapy, in a human or mammal.

DETAILED DESCRIPTION OF THE INVENTION

The present invention relates to pharmaceutical compositions and to methods for the prevention and attenuation of systemic disorders, acute and chronic neurological disorders, that involve the excessive activation of the NMDA receptor. Advantageously, the present invention relates to methods for neuroprotection in systemic and neurological disease through the administration of therapeutic compositions which contain, for example, the active ingredient 2-phenyl-1,3-propanediol dicarbamate, commonly known as felbamate. The compounds, such as felbamate, may be administered prophylactically, acutely, subacutely, or chronically via the intravenous, oral or rectal route. This compound has multiple mechanisms of action, one of which is a glycine-site antagonist at the NMDA receptor. Felbamate is able to inhibit the toxic effects of high glutamate concentrations while sparing the physiologic functions of the NMDA receptor, and thus can be safely administered chronically as monotherapy to humans.

Neuroprotection may be defined as increasing the tolerance of the glia and neurons of the brain and spinal cord to excessive NMDA activation which results in the prevention of neuronal cell death and promoting functional neuronal recovery, rather than just protecting neurons from ischemia (Fisher M., Stroke 25:1075–1080, 1994). Prophylactic neuroprotection will be administered to populations at high-risk for neuronal cell death. These would include (1) short term neuroprotection both prior to and post high-risk invasive, vascular or other procedures whose adverse event would produce neuronal injury or death, (2) chronic neuroprotection for high-risk populations with systemic disease or multiple cerebrovascular risk factors which increase the probability of neuronal cell injury or death, and (3) concomitant neuroprotection with other medications administered for specific systemic or neurological diseases which increase the risk for neuronal cell injury or death.

Several populations have a high long-term risk for neuronal cell injury or death which include vascular risk factors (such as obesity and hypertension), transient ischemic attacks, atrial fibrillation and other cardiac disorders, and asymptomatic carotid stenosis. In addition, there is a high risk of further additional neuronal cell injury or death after patients suffer a minor stroke. Patients with systemic diseases which increase the risk of neuronal cell injury or death have therapies directed specifically at the underlying disease and may require a concomitant neuroprotectant medication.

The short-term neuroprotection group includes patients undergoing vascular procedures such as coronary artery bypass graft surgery, carotid endarterectomy or other endovascular therapy which carry a high risk for embolic or ischemic complications resulting in neuronal cell injury or death. Depending on the individuals cerebrovascular risk factors, felbamate would be administered both pre- and post-procedure for a variable or chronic length of time.

The population for long-term felbamate administration would include patients with a high cerebrovascular risk-factor profile such as chronic hypertension, collagen vascular disease, atrial fibrillation, previous transient ischemic attack, etc.

The concomitant neuroprotection group includes those patients with a high cerebrovascular risk-factor profile from systemic disorders such as diabetes, hyperlipidemia, hypertension, collagen vascular disease, etc. in which felbamate is co-administered for neuroprotection with other medications which control and treat the underlying disease.

Compounds of the Invention

Compounds of the invention include felbamate, quinoxalinediones including the ACEA compounds (1011, 1021, 1031, 1328) ACPC (1-aminocyclopropane carboxylic acid), 1,4 dihydroquinoxaline-2,3-diones, 4-hydroxy-2-quinalones, 4-amino-2-carboxytetrahydro-quinolines, trans-4-hydropipecolic acid-4-sulfate, and other compounds whose mechanism of action includes at least glycine-site antagonism at the NMDA receptor Therapeutic Uses of the Compounds of the Invention Felbamate as monotherapy and other antagonists at the glycine site of the NMDA receptor are useful in the reduction or prevention of neuronal cell injury or cell death in systemic or neurologic diseases as well as patients with cerebrovascular risk factors, in which glutamate or other inflammatory neurotoxins and excitatory amino acids are involved in the pathophysiology. Felbamate is also useful for the treatment of spasticity due to its antagonism at the glycine-site at the NMDA receptor and its potentiation of GABA transmission.

Obesity

Obesity is a common human disorder which affects 10–15% of the population, of which up to 5% may be severely obese. It is estimated that the mortality from obesity is between 300,000 to 400,000 per annum. Obesity is commonly measured by the BMI (body mass index) which is the weight in kilograms divided by the height in meters squared. The degree of obesity is determined by comparisons against standard deviations above the means for males and females.

The male pattern of obesity is referred to as the android pattern in which the fat is distributed in the upper body while the female pattern is the gynecoid in which the body fat is distributed below the waist. These patterns appear to be related to the hormones testosterone and estrogen, respectively. Android obesity increases the risk of hypertension, cardiovascular disease, hyperinsulinemia, and diabetes mellitus.

The etiology of obesity is unknown but occurs when energy intake exceeds energy expenditure. Appetite is controlled by the ventromedial hypothalamus and complex interconnections with the limbic system and other portions of the brain. The amount of body fat has some genetic predisposition and rare genetic diseases such as Prader-Willi, syndrome, Laurence-Moon-Biedl syndrome, the Alstrom syndrome, the Cohen syndrome, the Carpenter syndrome, and Blount's disease are associated with obesity.

Complications of obesity include insulin resistance, diabetes mellitus, hypertension, cardiovascular disease, cerebral hemorrhage, pseudotumor cerebri, hyperlipidemia, respiratory problems, sleep apnea, venous circulatory disease, cancer, cholecystitis, and osteoarthritis.

Recent neurochemical research has implicated leptin, GLP-1 (glucagon-like peptide 1) and neuropeptide-Y in the control of appetite. Leptin is a natural appetite suppressant which is released from adipose cells, travels to the brain and appears to exert some control over appetite and long term weight control. A defective leptin receptor has been postulated to be involved in obese patients. GLP-1, a brain hormone which promotes satiety, is believed to regulate short-term appetite. Neuropeptide-Y is a potent stimulator of appetite whose effects can be blocked by leptin and GLP-1. The complete interaction of these compounds remains to be elucidated.

Felbamate has been known to induce anorexia in patients treated with epilepsy. In a study of felbamate as add-on therapy in partial epilepsy in children, weight loss was transient and returned to normal after twenty weeks (Carmant J., Pediatr 125:481–486, 1994). Weight loss of 4–5% was noted in patients on felbamate monotherapy (Faught E., Neurology 43:688–692, 1993). The mechanism is unclear and the weight loss has been attributed to nausea and vomiting and the withdrawal of other medications whose side effects are weight gain (Sachdeo R, Ann Neurol 32:386–392, 1992). We suggest a novel hypothesis that weight loss from felbamate is due to NMDA receptor modulation in the hypothalamic structures involved in appetite control.

Felbamate, administered chronically to humans in oral doses of from about 100–15,000 mg/day, advantageously from about 1200–7200 mg/day (serum levels ranging from about 25–300 ug/ml), is efficacious in producing weight loss in obesity, type-II diabetes, and other genetic obesity disorders. The weight loss will subsequently attenuate neuronal cell injury and death from the cerebrovascular complications of obesity.

Spasticity

Spasticity is a human motor disorder manifested by an increase in muscle tone and an exaggeration of deep tendon reflexes due to lesions of the corticospinal system. The spasticity is proportional to the rate and degree of stretch placed on the muscle. The most common causes are multiple sclerosis and spinal cord injury. Spasticity produces multiple medical complications, pain, and depression.

The etiology of spasticity is a decrease or malfunctioning of inhibitory mechanisms in the spinal cord leading to hyper-excitability of the tonic stretch and other reflexes. The mechanism may involve a decrease in both presynaptic GABA-ergic inhibition and postsynaptic inhibition. Noradrenergic receptors become supersensitive distal to spinal cord injury which is the rationale for using alpha-2 agonists as a treatment in spinal cord injury. GABA and glycine are the main inhibitory neurotransmitters in the spinal cord. Glycine acts at both the strychnine-insensitive and strychnine-sensitive receptors, the latter being more common in the spinal cord.

The pharmacotherapy of spasticity is directed at the potentiation of inhibitory transmission within the spinal cord, such as the mediation of presynaptic inhibition by GABA. Excitatory amino acids (EAA) increase spasticity and non-competitive NMDA antagonists depress spinal polysynaptic reflexes by inhibiting the release of EAA (Schwarz M., In Thilman AF, Ed. Spasticity, pp 85–97, 1993). Felbamate has both GABA enhancing properties and glycine-site strychnine insensitive antagonist properties which suggests efficacy in the treatment of spasticity.

Felbamate, administered chronically in oral doses of from about 100–15,000 mg/day, advantageously from about 1200–7200 mg/day (serum levels ranging from 25–300 ug/ml), is efficacious in reducing spasticity from both supraspinal and spinal lesions.

Symptomatic Depression

Depression or mood disorders are psychopathologic states in which a disturbance of mood is either a primary determinant or constitutes the core manifestation. Secondary depression is an affective disorder caused by a systemic or neurological disease. Examples of neurologic diseases include multiple sclerosis, Parkinson's disease, head trauma, cerebral tumors, post-stroke, early dementing illness, and sleep apnea etc. while systemic diseases include infections, endocrine disorders, collagen vascular diseases, nutritional deficiencies and neoplastic disease. Secondary depression is common in post-myocardial infarct patients and carry a mortality three times that of non-depressed post-myocardial patients.

Felbamate, administered chronically in oral doses of from about 100–15,000 mg/day, advantageously from about 1200–7200 mg/day (serum levels ranging from 25–300 ug/ml), is efficacious in reducing secondary symptomatic depression in both human systemic and neurologic diseases.

Post-Myocardial Infarction Neuroprotection

Patients with myocardial infarction are at a high risk for cardiac arrest resulting in global ischemia and causing neuronal injury, infarction and brain death. Other brain complications include cardiac embolism to the brain resulting in ischemic brain damage.

Felbamate has been to shown to be effective in preventing neuronal cell death when administered post-hoc (Wasterlain, C. G. Neurology 43:2303–2310, 1993; Shuaib, A. Brain Res. 727:65–70, 1996) as well as delayed cellular necrosis and delayed neuronal apoptosis in animal models of ischemia (Wasterlain, C. G., Stroke 27:1236–1240, 1996). These results show the efficacy of felbamate in preventing ischemic brain damage. All patients who have myocardial infarction are potentially at risk for global ischemia and cardiac embolism and should be placed on prophylactic felbamate to prevent and reduce neuronal cell death, delayed cellular necrosis and neural apoptosis.

Felbamate, administered chronically and prophylactically in oral doses of from about 100–15,000 mg/day, advantageously from about 1200–7200 mg/day (serum levels ranging from 25–300 ug/ml), is efficacious in preventing and reducing neuronal human cell injury and death from ischemia and embolism in patients with myocardial infarction.

Vascular Procedures

Certain invasive cardiovascular and peripheral vascular procedures are associated with a risk of both ischemic and embolic cerebrovascular damage. These procedures include coronary artery bypass graft surgery, cardiac valvular replacement, cardiac transplant, carotid endarterectomy, cerebral and peripheral aneurysmectomy, arterio-venous malformation resection, and endovascular therapy.

Felbamate administered pre- and post-vascular procedure would allow patients to have maximum neuroprotection prior to their exposure of such cerebrovascular risks.

Felbamate, administered acutely or chronically and prophylactically pre-vascular procedure and chronically post-vascular procedure in oral doses of from about 100–15,000 mg/day, advantageously from about 1200–7200 mg/day (serum levels ranging from 25–300 ug/ml), is efficacious in preventing and reducing neuronal human cell injury and death in patients undergoing central and peripheral vascular procedures.

Prophylaxis in Patients with Cerebrovascular Risk Factors

Several populations are at a high risk for insidious neuronal cell death, silent cerebral ischemia, and subsequent cerebral infarction. Individual risk factors, which may be present in various combinations, include hypertension, diabetes, atrial fibrillation, underlying cardiac disease, hyperlipidemia, collagen vascular disease, and transient ischemic attacks. A recent study has shown that asymptomatic hypertensive patients have evidence of cerebral neuronal degeneration (Salerno J. A., Hypertension 20:3340–348, 1992; Mentis M. J., Stroke 25:601–607, 1994). We hypothesize an up-regulation of cytokines which produce toxic inflammatory mediators such as the NMDA agonist quinolinic acid. This results in chronic overstimulation of the NMDA receptor producing neuronal cell death. Felbamate is a candidate for prophylactic neuroprotection since it is a glycine-site NMDA antagonist which easily crosses the blood brain barrier and can be safely administered chronically as monotherapy.

Felbamate, human administered prophylactically and chronically in asymptomatic patients with cerebrovascular risk factors in oral doses of from about 100–15,000 mg/day, advantageously from about 1200–7200 mg/day (serum levels ranging from 25–300 ug/ml), is efficacious in preventing and reducing neuronal cell injury and death in populations with cerebrovascular risk factors.

What is claimed is:

1. A method of treating a human suffering from obesity, the method comprising the steps of:

administering to said human in need of said treatment a neuronal cell protecting antagonist of the glycine site of the NMDA receptor complex, said antagonist being felbamate at a serum level ranging from about 25–300 $\mu$g/ml.

2. The method of claim 1, wherein said antagonist is 2-phenyl-1,3-propandeiol dicarbamate.

* * * * *